US010595792B2

(12) United States Patent
Shah

(10) Patent No.: US 10,595,792 B2
(45) Date of Patent: Mar. 24, 2020

(54) TOCODYNAMOMETER GPS ALERT SYSTEM

(71) Applicant: Riya Shah, Prospect, KY (US)

(72) Inventor: Riya Shah, Prospect, KY (US)

(73) Assignee: Fetal Life LLC, Prospect, KY (US)

(*) Notice: Subject to any disclaimer, the term of this patent is extended or adjusted under 35 U.S.C. 154(b) by 0 days.

(21) Appl. No.: 15/785,457

(22) Filed: Oct. 17, 2017

(65) Prior Publication Data
US 2018/0353142 A1 Dec. 13, 2018

Related U.S. Application Data

(60) Provisional application No. 62/517,986, filed on Jun. 11, 2017.

(51) Int. Cl.
*A61B 5/00* (2006.01)
*A61B 5/11* (2006.01)

(52) U.S. Cl.
CPC .......... *A61B 5/746* (2013.01); *A61B 5/1107* (2013.01); *A61B 5/4356* (2013.01); *A61B 5/6804* (2013.01); *A61B 5/6831* (2013.01)

(58) Field of Classification Search
CPC ... A61B 5/4356; A61B 5/1107; A61B 5/6831; A61B 5/0011; A61B 5/0022; A61B 5/4343
See application file for complete search history.

(56) References Cited

U.S. PATENT DOCUMENTS

| 5,042,503 A | 8/1991 | Torok et al. |
| 5,771,001 A * | 6/1998 | Cobb ............... A61B 5/0002 128/903 |
| 6,610,012 B2 | 8/2003 | Mault |

(Continued)

FOREIGN PATENT DOCUMENTS

| WO | 2007095457 A2 | 8/2007 |
| WO | 2007095457 A3 | 8/2007 |
| WO | WO-2019016759 A1 * | 1/2019 ......... A61B 5/04882 |

OTHER PUBLICATIONS

Aaronson et al., Android-Based Tocodynamometer and Fetal Heart Rate Monitor, Carnegie Mellon University BME Design, Spring 2014 Capstone Project, http://www.bme.cmu.edu/ugprog/design/2014Toco.pdf.

(Continued)

*Primary Examiner* — John Villecco
(74) *Attorney, Agent, or Firm* — Fitch, Even, Tabin & Flannery LLP

(57) ABSTRACT

The present development is a device for monitoring uterine activity and sending an alert signal through a wireless communication means when uterine activity significantly changes relative to a preset standard. The device, which comprises at least one sensor, is intended to continuously monitor a prescribed activity, such as uterine contractions. The information gathered by the sensors is fed to a computer application for comparison to preset values and, if the gathered information falls outside of the range of the preset values, feeds a signal to a second application designed to send out notifications to preprogrammed devices indicating the physical location of the source data, or where the pregnant patient is located.

13 Claims, 4 Drawing Sheets

(56) References Cited

U.S. PATENT DOCUMENTS

| | | | | |
|---|---|---|---|---|
| 7,154,398 | B2* | 12/2006 | Chen | G08B 25/016 340/573.1 |
| 7,261,691 | B1* | 8/2007 | Asomani | A61B 5/1112 128/920 |
| 8,313,447 | B2 | 11/2012 | Van Leer | |
| 8,874,773 | B2* | 10/2014 | Grube | H04W 4/90 709/230 |
| 9,119,602 | B2 | 9/2015 | Schafer | |
| 9,579,055 | B1* | 2/2017 | Rood | A61B 5/4362 |
| 9,585,614 | B2* | 3/2017 | Dugan | A61B 5/1075 |
| 9,629,340 | B2 | 4/2017 | Schab et al. | |
| 9,717,412 | B2* | 8/2017 | Roham | A61B 8/0866 |
| 9,763,621 | B1* | 9/2017 | Hafezi | A61B 5/6831 |
| 9,918,673 | B2* | 3/2018 | Dugan | A61B 5/1075 |
| 9,986,404 | B2* | 5/2018 | Mehta | H04W 4/029 |
| 9,998,507 | B2* | 6/2018 | Mehta | H04M 7/0057 |
| 10,419,915 | B2* | 9/2019 | Mehta | H04W 76/50 |
| 2002/0116080 | A1* | 8/2002 | Birnbach | A61B 5/0002 700/66 |
| 2002/0169584 | A1* | 11/2002 | Fu | A61B 5/16 702/188 |
| 2004/0225199 | A1* | 11/2004 | Evanyk | A61B 5/0002 600/300 |
| 2006/0047187 | A1* | 3/2006 | Goyal | A61B 5/1112 600/300 |
| 2009/0171166 | A1* | 7/2009 | Amundson | A61B 5/0002 600/301 |
| 2009/0171170 | A1* | 7/2009 | Li | A61B 5/00 600/301 |
| 2009/0299212 | A1* | 12/2009 | Principe | A61B 5/04882 600/547 |
| 2009/0322513 | A1* | 12/2009 | Hwang | A61B 5/02055 340/539.12 |
| 2011/0025493 | A1* | 2/2011 | Papadopoulos | A61B 5/02427 340/539.12 |
| 2011/0111736 | A1* | 5/2011 | Dalton | H04W 4/90 455/414.1 |
| 2012/0232398 | A1* | 9/2012 | Roham | A61B 8/0866 600/453 |
| 2012/0265090 | A1* | 10/2012 | Fink | A61B 5/0488 600/546 |
| 2013/0021154 | A1* | 1/2013 | Solomon | G08B 21/0453 340/539.12 |
| 2013/0158366 | A1* | 6/2013 | Bogineni | A61B 5/0002 600/301 |
| 2013/0197324 | A1* | 8/2013 | Waterhouse | A61B 5/0011 600/304 |
| 2013/0237861 | A1* | 9/2013 | Margarida | A61B 5/0006 600/483 |
| 2013/0307685 | A1* | 11/2013 | Sholder | G08B 21/02 340/539.12 |
| 2014/0207371 | A1* | 7/2014 | Johnson | A61B 5/1112 701/454 |
| 2015/0182160 | A1* | 7/2015 | Kim | A61B 5/0488 600/301 |
| 2015/0289822 | A1* | 10/2015 | Dugan | A61B 5/1075 600/301 |
| 2015/0351698 | A1* | 12/2015 | Cronin | A61B 5/0022 600/485 |
| 2015/0374328 | A1 | 12/2015 | Ginestet et al. | |
| 2016/0022227 | A1* | 1/2016 | Chen | H04M 1/72536 600/300 |
| 2016/0157717 | A1* | 6/2016 | Gaster | A61B 5/0444 600/301 |
| 2016/0270670 | A1* | 9/2016 | Oz | A61B 5/0245 |
| 2017/0049414 | A1* | 2/2017 | Venugopalan | A61B 8/02 |
| 2017/0143219 | A1* | 5/2017 | Ciecko | A61B 5/02438 |
| 2017/0172424 | A1* | 6/2017 | Eggers | A61B 5/0205 |
| 2017/0224268 | A1 | 8/2017 | Altini et al. | |
| 2017/0293730 | A1* | 10/2017 | Fish | A61B 7/003 |
| 2017/0325056 | A1* | 11/2017 | Mehta | H04W 4/90 |
| 2017/0337339 | A1* | 11/2017 | Cronin | G16H 50/30 |
| 2018/0000346 | A1* | 1/2018 | Cronin | G08B 21/0453 |
| 2018/0000405 | A1 | 1/2018 | Penders et al. | |
| 2018/0132778 | A1* | 5/2018 | Dugan | A61B 5/14542 |
| 2018/0199179 | A1* | 7/2018 | Rauner | H04W 4/90 |
| 2018/0317835 | A1* | 11/2018 | Groberman | A61B 5/0488 |
| 2018/0368753 | A1* | 12/2018 | Yin | A61B 7/00 |
| 2019/0012895 | A1* | 1/2019 | Myers | A61B 5/0022 |
| 2019/0328325 | A1* | 10/2019 | Parara | A61B 5/02438 |

OTHER PUBLICATIONS

Kumar et al., Smart Wearable Obstetric Assistant and Reminder—A Survey, Int'l J. Innovative Research in Science, Engineering and Technology, Jul. 2015, pp. 6420-6425, vol. 4, Issue 7.

Airstrip Technologies; Sense4Baby Privacy Policy; © 2019 AirStrip Technologies, This Policy is effective as of and was last updated on Nov. 30, 2015; https://www.airstrip.com/fetal-monitoring/privacy-policy; 6 pages.

T. Anderson; Fetal-Maternal Monitoring and Technology for Neonates; North Seattle College, rev cewood Jan. 19, 2018; http://facweb.northseattle.edu/cwood/EET287-Winter-2018/Presentations/Fetal-Maternal%20&%20Neonates-2018-01-19-complete.pdf; © 2014.

Dr. Rachel Hoad-Robson et al.; Cardiotocography; patient.info/health/cardiotocography; Aug. 31, 2016; 3 pages.

Whitney Aaronson et al.; Android-Based Tocodynamometer and Fetal Heart Rate Monitor; Spring 2014; 14 pages.

* cited by examiner

TOCODYNAMOMETER GPS ALERT SYSTEM

CROSS-REFERENCE TO PRIOR APPLICATIONS

The present application claims priority to U.S. patent application Ser. No. 62/517,986 filed 2017 Jun. 11, which is incorporated by reference in its entirety.

FIELD OF THE INVENTION

The invention relates to a system for determining if a pregnant woman has entered first stage labor and, at the onset of the first stage of labor, for notifying designated persons that labor has commenced and sharing the global positioning system coordinates of the person in the labor.

BACKGROUND OF THE INVENTION

Childbirth is the ending of a pregnancy by the delivery of one or more babies. Delivery may occur through a vaginal delivery or by Caesarian section (C-section). An expectant mother who will deliver by C-section is normally scheduled for surgery on a specific date and therefore can notify her spouse, family, friends, and obstetrician in advance of the surgical date. But a woman who anticipates a vaginal delivery is dependent on changes in her own body to indicate when the baby will arrive.

Vaginal delivery involves three stages of labor. The first stage is the shortening and opening of the cervix, the second stage is the descent and birth of the baby, and the third stage is the delivery of the placenta. If a hospital birth is planned, it is common practice for the expectant mother to go to the hospital during the first stage of labor; or if a home birth is planned, the midwife or birth attendant is normally called to begin attending to the expectant mother during the first stage of labor.

The first stage is normally defined as the point at which the woman perceives regular uterine contractions. The challenge is determining if the uterine contractions are occurring at regular intervals. Varying degrees of cramping or pain associated with each contraction may make it difficult to accurately assess the time, or interval, between contractions. Further, the expectant mother may dismiss early first stage contractions because of prior experience with Braxton Hicks contractions or "false labor". Braxton Hicks contractions are contractions that are usually infrequent, regular, and involve only mild cramping that may start around 26 weeks gestation. In addition, the first stage of labor typically lasts from about twelve hours to about twenty hours, so it can be challenging for the expectant mother to know when to contact medical personnel and family members to her aid. Finally, because we live in a highly mobile society, the expectant mother may not be at or near home or a similar base location when the time first stage labor has reached the point when she needs medical assistance, so it may be challenging for contacted personnel to locate the expectant mother.

Efforts have been made to monitor when first stage labor begins by using tocodynamometers. The tocodynamometer operates by using a pressure transducer applied to the fundus of the uterus by means of a belt. The transducer is connected to a recording device that records the duration of the contractions and intervals between them. These devices, however, require the expectant mother to be physically still for extended periods of time to allow for accurate readings. Because of this and because the current devices use cumbersome recording devices, the prior art tocodynamometers are normally used to monitor the expectant mother's contractions for at most a couple hours each day and only in high-risk pregnancies.

It would be beneficial for expectant mothers to have an easy to use means to essentially continually monitor for the onset of first stage labor in the final trimester of pregnancy, including allowing the expectant mother to be mobile while using the monitoring means. It would further be beneficial to have the monitoring means configured to alert the expectant mother that labor has reached the point of requiring medical assistance and to alert those designated by the expectant mother that labor has reached the point of requiring medical assistance along with providing a designation of the physical location of the expectant mother at the time of alert.

SUMMARY OF THE PRESENT INVENTION

The present development is a labor alert system for determining if a pregnant woman has entered first stage labor and, if first stage labor has started, for sending messages to preselected devices. The labor alert system comprises a device for monitoring uterine activity and for assessing whether the uterine activity has progressed to first stage labor, and a means for sending an alert signal through a wireless communication system when uterine activity significantly changes relative to a preset standard. The device for monitoring uterine activity is intended to be positioned on the exterior surface of a pregnant patient's abdomen, and has one or more sensors to continuously monitor uterine contractions. When first stage labor is detected, the location of the uterine activity monitoring device is detected and the location is transmitted to preselected mobile devices that have pre-installed an alert application.

More specifically, the tocodynamometer GPS alert system of the present invention comprises a uterine activity transducer, a means to secure the uterine activity transducer against the pregnant patient's fundus or abdomen, a means to electronically transmit data gathered by the uterine activity transducer to a data processing application wherein the data processing application is designed to differentiate uterine activity, such as muscle contractions and movements, that represents non-first-stage labor from activity that represents first-stage labor, and wherein the data processing application is further designed to send a signal to an alert application if and only if the first-stage labor has commenced or the pregnant patient is in medical distress. The alert application is further designed to determine the location of the uterine activity transducer and to send out a signal to preselected communication devices indicating that first stage labor has commenced or the patient is in distress and indicating the location of the uterine activity transducer. In an alternative embodiment, the alert application may further include functionalities to identify the closest hospital or emergency care facility and to provide that information to the pregnant woman and/or to allow the pregnant woman to activate an alert for emergency help and to provide the coordinates for the location of the tocodynamometer GPS alert system to the nearest emergency provider and/or to allow the pregnant woman to directly enter data regarding her condition to the data processing application. Because the tocodynamometer GPS alert system is mobile and easy to use, it can improve the quality of life for the pregnant woman in her third trimester of pregnancy.

DETAILED DESCRIPTION OF THE PRESENT DEVELOPMENT

Figure 1:
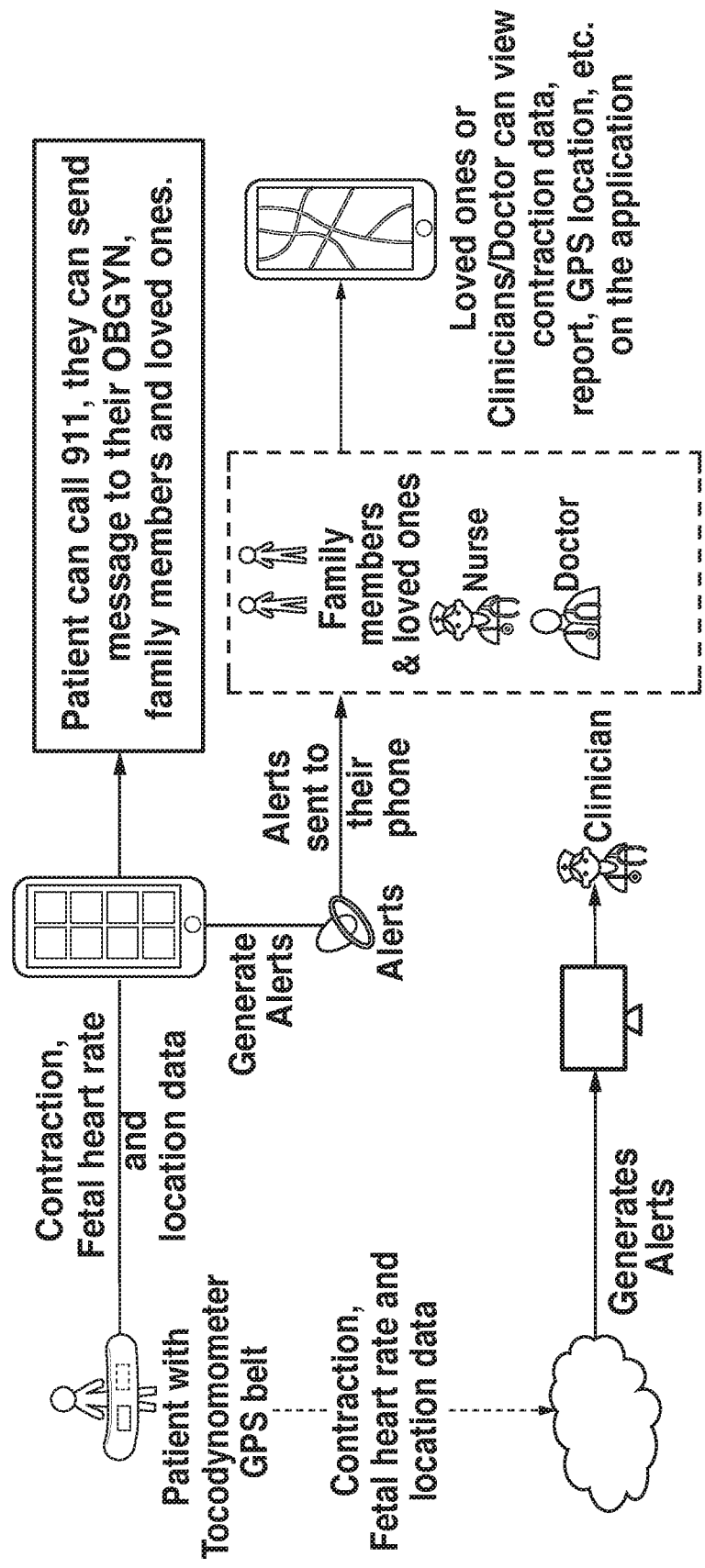
FIG. 1 is a highly-simplified communication diagram for an exemplary embodiment of the labor alert system of the invention.

The following description is intended to provide the reader with a better understanding of the invention. The description is not intended to be limiting with respect to any element not otherwise limited within the claims. For example, the present invention will be described in the context of use with a commonly known cellular telephone, but the teachings herein are not limited to currently available cellular telephones and are anticipated to be adaptable to other mobile communication devices without departing from the scope of the invention.

The present development is a labor alert system for the remote monitoring of a pregnant woman's physical condition and for determining if a pregnant woman has entered first stage labor or is in medical distress and, at the onset of the first stage of labor or distress, for notifying designated persons—or more specifically for sending information to preselected electronic devices—indicating that labor has commenced and for sharing the global positioning system ("GPS") coordinates specifying the location of the pregnant woman. The labor alert system or uterine activity monitoring system, which will be referred to herein as a "tocodynamometer GPS alert system", comprises a patient monitor and a means for sending an alert signal through a wireless communication system when uterine activity significantly changes relative to a preset standard. The patient monitor comprises a device for monitoring uterine activity and for assessing whether the uterine activity has progressed to first stage labor, and a means for determining the GPS coordinates of the device for monitoring uterine activity. The labor alert system of the present invention relies on the physical changes that occur in an expectant woman's body as delivery of her baby becomes imminent and, in particular, changes that occur during the first stage of labor when relatively strong uterine contractions begin to occur at regular intervals and/or in changes that occur to the fetus as delivery approaches or uterine conditions change.

In one embodiment, the tocodynamometer GPS alert system of the present invention is a labor alert system for remote monitoring of the progress of first stage labor in a pregnant patient comprising (1) a uterine activity monitoring device comprising (a) a uterine activity transducer containing at least one uterine activity monitor configured to detect a preselected uterine activity and to produce uterine activity signals and a means to electronically transmit data gathered by the uterine activity transducer to a data processing application, (b) a means for determining the physical location of the device for monitoring uterine activity, and (c) a means to secure the uterine activity transducer against a pregnant patient's fundus or abdomen; (2) a processor comprising (a) a first data processing application for receiving data from the uterine activity transducer, wherein the first data processing application corrects said uterine activity signals for distortion caused by other movement signals to produce corrected uterine activity signals and wherein the first data processing application evaluates whether the uterine activity has progressed to first stage labor by comparing real-time corrected uterine activity signals with pre-labor baseline uterine activity signals, and wherein the first data processing application transmits a signal to a second data processing application if the differential between the real-time corrected uterine activity signals and the pre-labor baseline uterine activity signals exceeds a predetermined value, and (b) a second data processing application for receiving data from the means for determining the physical location of the device and from the first data processing application if the differential between the real-time corrected uterine activity signals and the pre-labor baseline uterine activity signals exceeds a predetermined value, and wherein the second data processing application transmits an alert signal to at least one receiver; and, (3) at least one receiver for receiving the alert signal from the second data processing application, wherein the alert signal specifies that first stage labor or a medical distress condition has commenced and the physical location of the uterine activity monitoring device, wherein the uterine activity monitoring device is reversibly fitted on the pregnant patient and the processor is in wireless communication with the uterine activity monitoring device and the receiver is in wireless communication with the processor. The uterine activity monitored may be uterine muscle contractions or fetal movement or fetal heart rate or a combination thereor, or any other physical parameter or combination of physical parameters that can be monitored non-intrusively. The means for determining the physical location of the device for monitoring uterine activity may be a global positioning system (GPS) or any system that can determine the geographic coordinates of the monitoring device. The receiver may be a remote patient management website or a mobile electronic device running pregnancy monitoring software or a cellular phone or an electronic tablet or a combination thereof. Optionally, the receiver may be configured to enable the pregnant patient to input data indicative of the pregnant patient's status.

The labor alert system of the present invention represents improvements over the prior art wherein the improvements comprise a means for determining the physical location of the device for monitoring uterine activity and a means for receiving data from the means for determining the physical location of the device and combining the data from the means for determining the physical location with the data from the uterine activity transducer and then sending an alert signal to at least one preselected device. Relative to the prior art, the present invention also represents an improvement by being mobile and easy to use at the user level, i.e. the system of the present invention is not limited to clinical or medical facility use and does not require any special set up to use.

The present invention is also a method for remote monitoring of the progress of first stage labor in a pregnant patient comprising (1) providing a uterine activity monitoring device comprising (a) a uterine activity transducer containing at least one uterine activity sensor, (b) a means for determining the physical location of the device for monitoring uterine activity, and (c) a means to secure the uterine activity transducer against a pregnant patient's fundus or abdomen; (2) providing a processor comprising a first data processing application for receiving data from the uterine activity transducer and a second data processing application for receiving data from the means for determining the physical location of the device and from the first data processing application, and providing at least one receiver for receiving the alert signal from the second data processing application, wherein the uterine activity monitoring device is reversibly fitted on the pregnant patient and processor is in wireless communication with the uterine activity monitoring device and the receiver is in wireless communication with the processor, and wherein the uterine activity transducer is secured against the patient's fundus or abdomen and the uterine activity of the pregnant patient is monitored and recorded as uterine activity signals by the uterine activity transducer and the physical location of the patient is monitored and recorded as global positioning system coordinates by the means for determining the physical location of the device for monitoring uterine activity and wherein the uterine activity signals are transmitted to the first data processing application wherein the first data processing application corrects said uterine activity signals for distortion caused by pre-labor baseline uterine activity signals to produce corrected uterine activity signals and wherein the first data processing application evaluates whether the uterine activity has progressed to first stage labor or fetal distress by comparing real-time corrected uterine activity signals with the pre-labor baseline uterine activity signals, and wherein the first data processing application transmits a signal to the second data processing application if the differential between the real-time corrected uterine activity signals and the pre-labor baseline uterine activity signals exceeds a predetermined value and wherein the global positioning system coordinates are transmitted to the second data processing application and wherein the second data processing application transmits an alert signal comprising the GPS coordinates and a message that first stage labor or fetal distress has commenced to the at least one receiver if the differential between the real-time corrected uterine activity signals and the pre-labor baseline uterine activity signals exceeds a predetermined value.

FIG. 1 is a highly-simplified communication diagram for carrying out the process of the invention. As shown in FIG. 1, a patient wears the patient monitor during pregnancy. The patient's uterine activity and global positioning coordinates are routinely monitored. When the uterine activity reach a predetermined threshold specific for that patient, alerts are triggered which are visible to the patient and messages are sent to devices pre-programmed with an alert application, such as mobile phones of family members, physicians, attending nurses and/or midwives, indicating that labor has begun or the fetus is in medical distress and letting the message recipient know the patient's GPS coordinates, which can be translated to the patient's physical location through methods known in the art. Alternatively, the patient's uterine activity and global positioning coordinates can be routinely monitored and the data can be stored in a remote storage location, such as a cloud storage, and when the activity reaches a predetermined threshold specific for that patient, alerts are triggered which are visible to the patient and messages are sent to devices pre-programmed with a recipient alert application indicating that labor has begun or the fetus is in medical distress and letting the message recipient know the patient's physical location. Optionally, the recipients of the notifications may be able to access further data about the patient's condition, such as essentially real-time contraction data or fetal heart rate, from the cloud storage. In a preferred embodiment, the alert application may further include functionalities to allow the patient to interact with the alert system to directly send messages to specific individuals, such as family members or the patient's physician, or to allow the patient to contact 911 or to activate an alert for emergency help, optionally with the alert application providing the nearest emergency provider with the coordinates for the location of the patient monitor, or to identify the closest hospital or emergency care facility and to provide that information to the patient, or a combination thereof.

Figure 2:
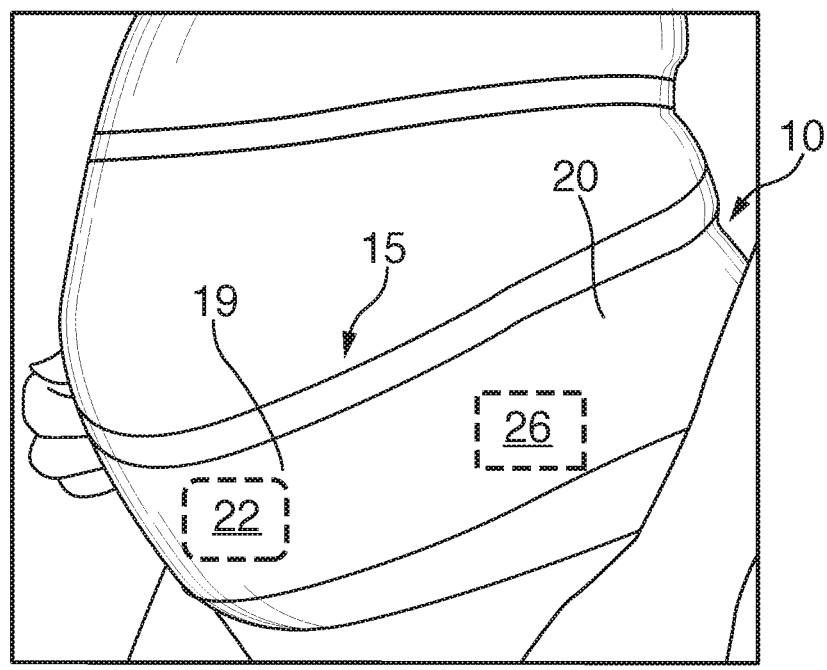
FIG. 2 is a front perspective of a uterine activity monitoring device for use in the labor alert system of the invention with the uterine activity monitoring device shown as it is intended to be used.

As shown in FIG. 2, the tocodynamometer GPS alert system 10 comprises a patient monitor 15, intended to be positioned on the exterior surface of a pregnant patient's fundus or abdomen, and a means for sending an alert signal through a wireless communication system (not shown) when uterine activity significantly changes relative to a preset standard. The patient monitor 15 comprises a device for monitoring uterine activity or a uterine activity transducer 22, many styles and variations of which are known in the art such as, without limitation, one or more sensors or electrodes, and a means for determining the GPS coordinates of the device for monitoring uterine activity 26. More specifically, the tocodynamometer GPS alert system 10 of the present invention comprises a belt 20 or an elasticized garment or an adhesive strip or any other means to secure the uterine activity contraction transducer against the pregnant patient's abdomen, the uterine transducer 22, a means for converting data received from the transducer to a digital display (not shown), an output display 24 (not shown) and the global positioning system ("GPS") tracker 26. The belt 20 has an exterior face 19 and an interior face 21 (not shown). The means for converting data received from the transducer to a digital display may be located within the belt 20 or may be located at a remote location that is in communication with the belt 20 or may be a combination thereof. The output display 24 may be positioned on the belt 20 or may be a separate unit, such as a cellular phone or electronic tablet. Optionally, the means for converting data received from the transducer to a digital display may further include a means for converting data to a patient alert mode, such as causing a light located on the belt to illuminate or creating a slight vibrating signal or causing an audible alert or beeping sound.

For the purposes of demonstrating the invention, the tocodynamometer GPS alert system will be described herein as using an elasticized band that wraps around the patient's lower torso to secure the uterine activity transducer against the pregnant patient's abdomen. However, the tocodynamometer GPS alert system would function as intended as long as the uterine activity transducer was secured against the pregnant patient's abdomen. This could be accomplished by permanently affixing the transducer to a garment worn by the patient, or by providing a pocket or pouch within a garment to be worn by the patient wherein the patient could insert the transducer reversibly within the pocket or pouch thereby allowing the patient to launder the garment, or by securing the transducer to a pouch or packet that could be secured directly to the patient's skin by adhesive, or by a combination thereof.

Figure 3:
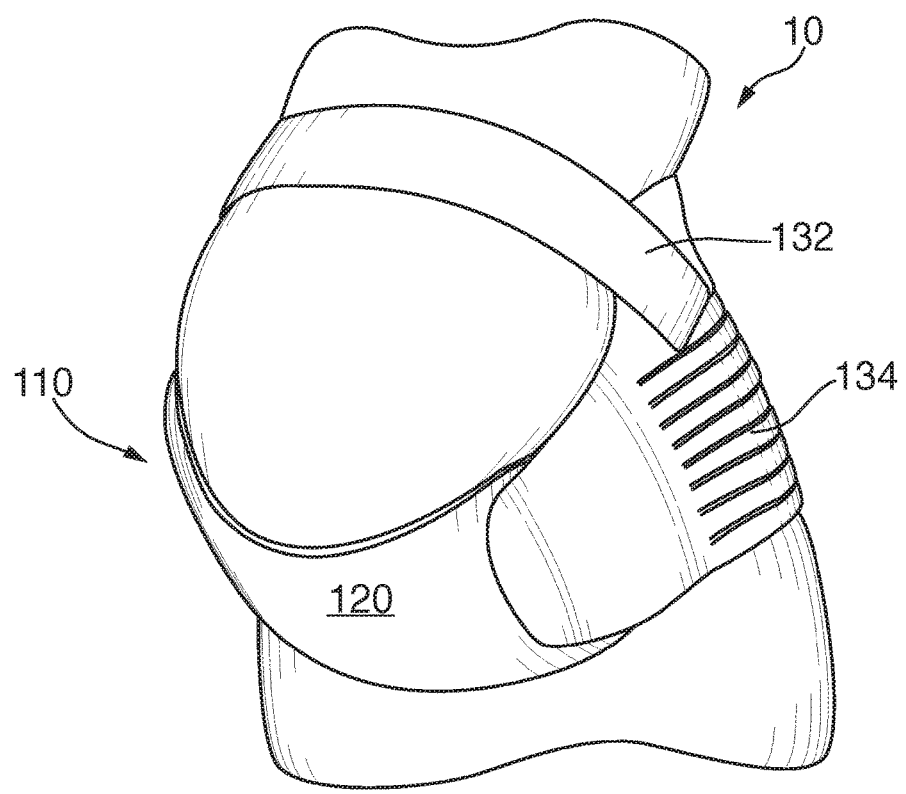
FIG. 3 is a front perspective of a first alternative embodiment of a uterine activity monitoring device for use in the labor alert system of the invention and shown as it is intended to be used.
Figure 4:
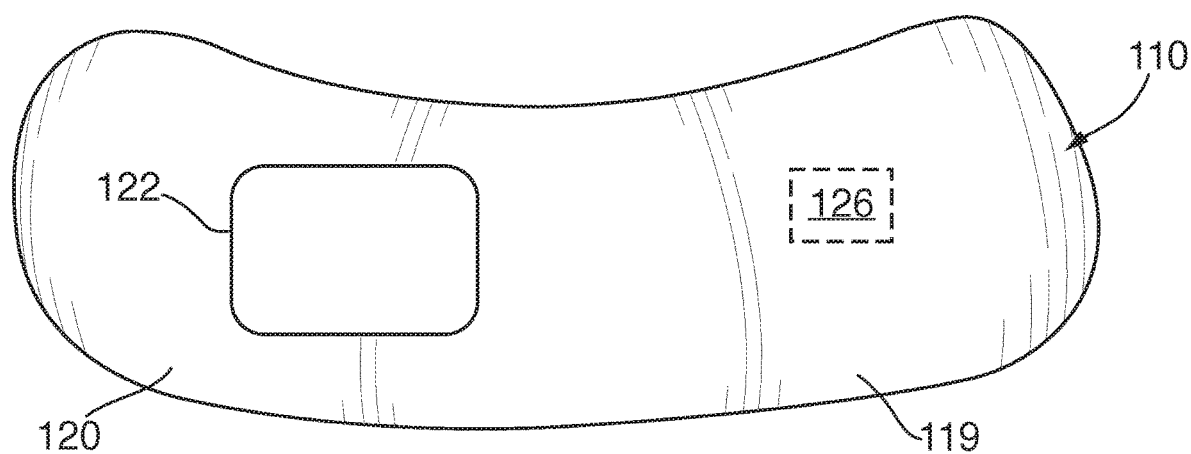
FIG. 4 is front view of the uterine activity monitoring device of FIG. 3.
Figure 5:
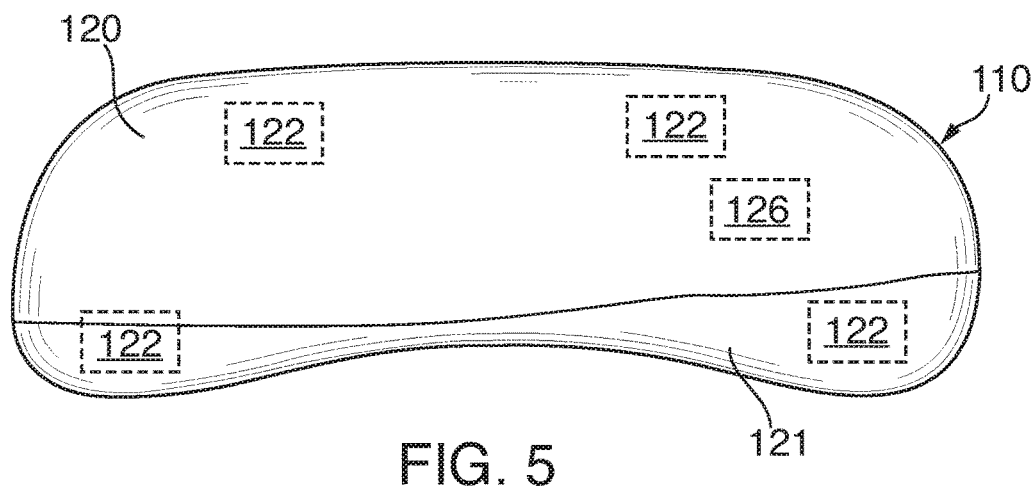
FIG. 5 is a rear view of the uterine activity monitoring device of FIG. 3.

A first alternative embodiment of the tocodynamometer GPS alert system 110 is shown in FIGS. 3-5. The belt 110 is essentially identical to belt 10 except the belt 110 includes an optional support strap 132 and an optional back support panel 134. As shown in FIGS. 3-5, the tocodynamometer GPS alert system 110 comprises a belt 120, having an exterior face 119 and an interior face 121, a uterine activity monitor 122 which may comprise one or more sensors or electrodes as is known in the art, a means for converting data received from the uterine activity monitor to a digital display (not shown), an output display 124 and a GPS tracker 126. The support strap 132 and back support panel 134 can help to stabilize the tocodynamometer GPS alert system 110, but are not required for the belt 110 to function as intended.

The uterine activity monitor 22, 122 of the tocodynamometer GPS alert system 10, 110, is designed to continuously monitor a prescribed activity, such as uterine contractions or fetal heart rate or maternal heart rate or frequency of fetal "kicks" or a combination thereof. The data collected by the monitor is transmitted to the means for converting data received from the monitor to a digital display, such as an analog-to-digital (A/D) converter (not shown) so the analog output from the sensors 22, 122 can be converted to a digital output. Analog-to-digital (A/D) converters are well-known in the art and any A/D converter that can accept input from the monitor 22, 122 and provide output in digital form may be used in the tocodynamometer GPS alert system 10, 110.

The labor alert system of the present invention further includes a means to electronically transmit data received from the uterine activity transducer or the sensors to a data processing application designed to compare the sensor data to a set of preset threshold values or to differentiate muscle contractions and movements that represent non-first-stage labor from muscle contractions and movements that represent first-stage labor. The preset threshold values may be based on statistical averages from the general population or may be specific to the patient. For example, the processing application may be designed to record and establish a "baseline" for the patient and to compare real-time input to the individual patient's baseline values. The patient's baseline may be adjusted as the pregnancy progresses, such as the patient's medical caretaker may revise the preset thresholds after reviewing the patient's medical records or the patient may provide feedback indicating a temporary anomaly or the processing application may be designed to include an "artificial intelligence" feature that can analyze changes in the patient's status over varying periods of time or at different times of day or when the patient is located within a particular geographic area or that can include algorithms that include analyzing a predetermined combination of the individual patient's physical factors, such as pain level changes or changes in fetal heart rate or changes in maternal heart rate, and that can predict the patient's risk level or estimate the patient's delivery date, or a combination thereof. If the sensor-derived value falls outside of the range of the preset values, indicating that first-stage labor has commenced or that the patient may otherwise be at risk, the data processing application locates the position of the GPS tracker 26, 126 or causes a second application to locate the position of the GPS tracker 26, 126, and the GPS tracker information is transmitted to a sender alert application or the application may be designed to send out notifications to preprogrammed electronic devices. In a preferred embodiment, the preprogrammed devices will display a customized message or send a customized e-mail message, such as "Mary is in labor", along with the patient's GPS coordinates that can be shared with patient's loved ones. Optionally, the GPS coordinates can be opened in a GPS application to show more details. In a more preferred embodiment, the preprogrammed message will update on a defined schedule, such as every fifteen (15) minutes, so the recipient of the message can be aware of any changes in status. For example, the initial message may read "Mary is in labor." along with the location details and 15 minutes later the message may read "Mary is in labor." with new GPS location details. In a most preferred embodiment, the message will include a link to the GPS tracker so the recipient of the message can use any GPS-accommodating programs and determine the exact location of the tocodynamometer GPS alert system 10, 110.

Optionally, the data processing application may be further designed to assess the differential between the data collected by the monitor 22, 122 and the preset threshold values, and if the differential exceeds a predetermined value the data processing application may be designed to feed a signal to an emergency responder application designed to call emergency services or 911 and to notify the emergency service of the location of the GPS tracker. In addition, the data processing application may be programmed to allow the patient to directly link to 911 or an emergency response center or to the patient's physician. In a preferred embodiment, the application will indicate the location of the closest hospital or the closest physician's office relative to the patient's location.

In alternative embodiments of labor alert system, the patient and/or the recipients may enter data into the database to supplement data received from the monitor. For example, in a first alternative embodiment, the application may include an option that allows the patient to enter a "pain" value, for example entering 1 would indicate mild pain whereas entering 10 would indicate severe pain; and the patient's pain level may then be correlated to the sensor-detected contraction strength. The data processing application could be designed to add the patient's pain level to the patient's records, and the threshold for sending notifications to other preprogrammed devices may be based on an algorithm that combines the frequency of the patient's uterine contractions and the patient's reported pain level. In a second alternative embodiment, the recipients may have an option to enter a "delivery date pool" where each person may guess the date and/or time the baby will be delivered.

Figure 6:
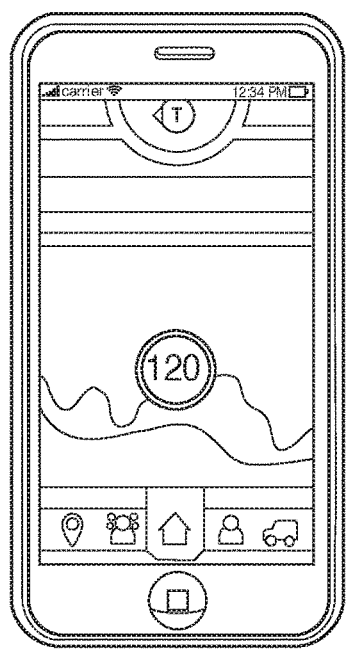
FIG. 6 is a screen shot of an exemplary mobile device display on a device that has downloaded a recipient alert application designed for use in the labor alert system of the present invention.
Figure 7:
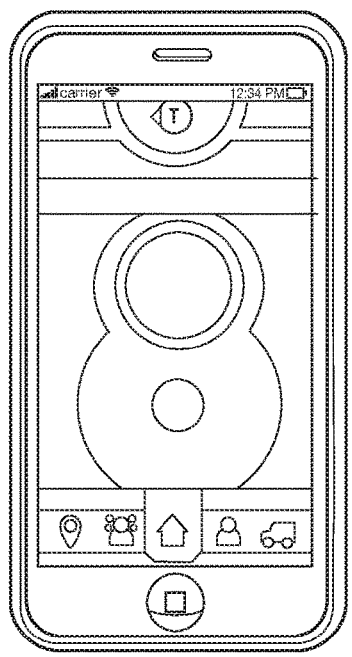
FIG. 7 is a screen shot of a first alternative mobile device display on a device that has downloaded a recipient alert application designed for use in the labor alert system of the present invention; and, FIG. 8 is a screen shot of a second alternative mobile device display on a device that has downloaded a recipient alert application designed for use in the labor alert system of the present invention.
Figure 8:
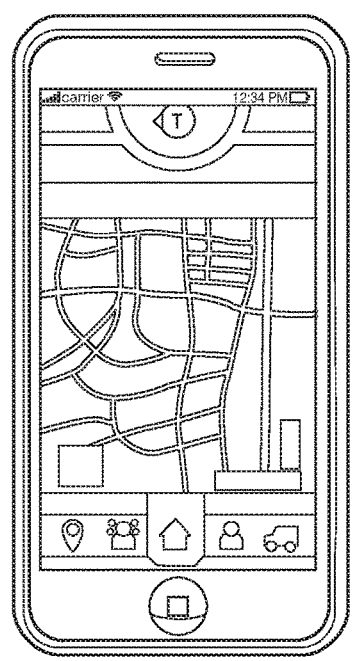

The labor alert system of the present invention is intended to be used in conjunction with mobile electronic devices, such as smartphones, tablets and similar electronic communication devices. As is known in the art, these types of devices can download applications to perform various functions, such as to provide directions from one location to another using GPS coordinates or to provide local traffic condition information or to provide local weather conditions and forecasts. In order for a particular mobile electronic device to receive a notification from the labor alert system of the present invention, the owner of the mobile electronic device would need to download a recipient's alert application. The recipient's alert application would link with the sender alert application to provide information about the patient. Exemplary screenshots of the output from the recipient's alert application are shown in FIGS. 6-8. For example, the information displayed on the mobile device may provide information about the patient's physical condition, such as fetal heartrate (FIG. 6), or the status of calls being made (FIG. 7), or the location of the tocodynamometer GPS alert system (FIG. 8). The information displayed may be determined by the programming of the recipient's alert application and may allow the individual recipient to opt-in or opt-out of certain functions or may allow the patient to control what information can be accessed by any particular recipient. For example, the patient would be able to assign certain privileges within the sender alert application which would dictate what functionality each individual recipient would have, so while all recipients may be alerted that the patient was in labor and to see the patient's physical location only the patient's spouse and physician would have access to the patient's physical condition.

In an exemplary embodiment of the invention, the patient monitor 22 is a pressure-sensing transducer secured to the interior face 21 of the belt 20. As is known in the art, a pressure sensing transducer can detect uterine contractions of an expectant mother, even those mild enough that they cannot be felt by the mother herself. As uterine contractions occur, an analog output voltage, corresponding to the intensity of the contractions, is generated by the pressure sensing transducer. If necessary, the output may be amplified using techniques known in the art. When the—output exceeds a predefined threshold level, reflecting a contraction of significant intensity, a mark is recorded and an internal timer automatically starts, and then the sensor returns to monitoring the output level. If the output level does not again exceed the predefined threshold level within thirty minutes of the immediately preceding mark recording, the timer resets to zero and the monitoring procedure continues with no alerts or notifications. However, if the output level exceeds the predefined threshold level within thirty minutes of the immediately preceding mark recording, a signal is sent to an alarm on the display 24 indicating that first stage labor may be commencing, and the internal timer resets to zero and the monitoring procedure repeats itself. If the output again exceeds the predefined threshold within thirty minutes of the immediately preceding mark and within sixty minutes of the two most recently immediately preceding mark, a second signal is sent to an alarm on the display 24 indicating that first stage labor may be commencing and a third signal is sent to an application programmed to ascertain where the GPS tracker 26 is located and to send out a message to preselected communication devices indicating that first stage labor has commenced and indicating the location of the GPS tracker 26.

In a preferred embodiment, the belt 20, 120 will be made from an elastic-type fabric or a material that will feel comfortable against the skin but will hold the transducer tightly against the skin without constricting blood flow in the area. In a more preferred embodiment, the belt will include a liner on the interior face 21, 121 that will minimize the transmission of any radiation to the abdominal area of the expectant mother.

It is anticipated that the applications referenced herein that compare output from the patient monitor 22, 122 and that cause information to be displayed on the display 24, 124 and that cause messages to be sent to preselected communication devices may be designed for any computer-based platform and may include a variety of data transfer options, such as but not limited to use of SIM cards to store data or to transfer data directly to cloud storage. It is further anticipated that the preselected communication devices may be any type of device that can run a computerized application, such as but not limited to cellular telephones, smartphones, or tablets, and that the means for transmitting the data and messages may be any means known in the art, including but not limited to service buses, event hubs, IoT (Internet of Things) hubs, and the like.

Because the tocodynamometer GPS alert system does not require any special set-up, such as specialized software only available to medical personnel, is mobile and is easy to use, it can improve the quality of life for the pregnant woman in her third trimester of pregnancy.

Unless defined otherwise, all technical and scientific terms used herein have the same meaning as commonly understood by one of ordinary skill in the art to which the presently disclosed subject matter pertains. Representative methods, devices, and materials are described herein, but are not intended to be limiting unless so noted.

The terms "a", "an", and "the" refer to "one or more" when used in the subject specification, including the claims.

Unless otherwise indicated, all numbers expressing quantities of components, conditions, and otherwise used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to a measurement or to an amount of mass, weight, time, volume or percentage can encompass variations of, in some embodiments ±20%, in some embodiments ±10%, in some embodiments ±5%, in some embodiments ±1%, in some embodiments ±0.5%, and in some embodiments to ±0.1%, from the specified amount, as such variations are appropriate in the disclosed application.

Specific dimensions relevant to the tocodynamometer GPS alert system described herein are provided herein for the purpose of demonstrating the invention, but these dimensions are not intended to limit the scope of the invention. It is understood that, in light of a reading of the foregoing description, a person with ordinary skill in the art may make alterations and/or modifications to the present invention, and specifically to the embodiments shown and described herein, without departing from the scope of the invention. For example, those skilled in the art may substitute materials supplied by different manufacturers than specified herein without altering the scope of the present invention.

What is claimed is:

1. A labor detection and alert system comprising:
   a uterine activity transducer configured to, when mounted against a pregnant patient's abdomen, detect uterine activity of the pregnant patient and provide a corresponding uterine activity signal;
   an attachment member configured to secure the uterine activity transducer against the pregnant patient's abdomen;
   a global positioning system (GPS) tracker disposed to track a location of the pregnant patient;
   a control circuit coupled to the uterine activity transducer and the GPS tracker and configured to:
   detect when the pregnant patient begins first stage labor as a function of the uterine activity signal;
   determine a location of the pregnant patient as a function, at least in part, of information provided by the GPS tracker; and upon detecting that the pregnant patient has begun first stage labor, responsively cause a transmission of a wireless alert message to a plurality of predetermined recipients to specifically represent that first stage labor has begun for the pregnant patient, wherein the wireless alert message also includes location information corresponding to a location of the pregnant patient, such that the plurality of predetermined recipients are informed of the pregnant patient's location at a time when the first stage labor began, and wherein the control circuit is further configured to, upon detecting that the pregnant patient has begun first term labor, responsively cause a transmission of a different wireless alert message to at least one other predetermined recipient that is different than the plurality of predetermined recipients to specifically represent that first stage labor has begun for the pregnant patient, wherein the different wireless alert message does not include the location information.

2. The labor detection and alert system of claim 1 wherein the plurality of predetermined recipients constitutes a spouse for the pregnant patient and at least one medical services provider.

3. The labor detection and alert system of claim 1 wherein the control circuit is further configured to, subsequent to detecting that the pregnant patient has begun first stage labor, cause a transmission of a wireless update message to the at least one predetermined recipient that at least includes current location information corresponding to a current location of the pregnant patient.

4. The labor detection and alert system of claim 3 wherein the control circuit is configured to cause transmissions of updated wireless update messages in accordance with a defined schedule.

5. The labor detection and alert system of claim 4 wherein the defined schedule comprises increments of 15 minutes.

6. The labor detection and alert system of claim 4 wherein at least some of the updated wireless update messages include a preprogrammed message.

7. The labor detection and alert system of claim 6 wherein the preprogrammed message includes textual content.

8. The labor detection and alert system of claim 7 wherein the textual content includes a name of the pregnant patient.

9. The labor detection and alert system of claim 1 wherein the control circuit is further configured to respond to detection of the pregnant patient actuating an emergency alert interface.

10. The labor detection and alert system of claim 9 wherein the control circuit is configured to respond to detection of the pregnant patient actuating the emergency alert interface by providing a nearest emergency medical services provider with location information corresponding to the pregnant patient.

11. The labor detection and alert system of claim 9 wherein the control circuit is configured to respond to detection of the pregnant patient actuating the emergency alert interface by providing information to the pregnant patient that identifies a closest emergency medical services provider.

12. The labor detection and alert system of claim 1 wherein the control circuit comprises a part of a multifunction mobile communications device.

13. The labor detection and alert system of claim 12 wherein the multifunction mobile communications device comprises a smart phone.

* * * * *